United States Patent [19]

Schilling, Jr.

[11] 4,160,775

[45] Jul. 10, 1979

[54] PROCESS FOR THE PREPARATION OF NOVEL ORGANOSILICON COMPOUNDS

[75] Inventor: Curtis L. Schilling, Jr., Croton-on-Hudson, N.Y.

[73] Assignee: Union Carbide Corporation, New York, N.Y.

[21] Appl. No.: 890,970

[22] Filed: Mar. 28, 1978

[51] Int. Cl.$^2$ .................................................. C07F 7/08
[52] U.S. Cl. ...................... 260/448.2 E; 260/448.8 R
[58] Field of Search .................. 260/448.2 E

[56] References Cited

U.S. PATENT DOCUMENTS

| | | | |
|---|---|---|---|
| 2,823,218 | 2/1958 | Speier et al. | 260/448.2 E |
| 2,970,150 | 1/1961 | Bailey | 260/448.2 E X |
| 3,842,112 | 10/1974 | Omietanski et al. | 260/448.2 E X |
| 3,957,843 | 5/1976 | Bennett | 260/448.2 E X |
| 4,059,605 | 11/1977 | Bennett | 260/448.2 E X |

*Primary Examiner*—Paul F. Shaver
*Attorney, Agent, or Firm*—Richard J. Gallagher

[57] ABSTRACT

Organic compounds having the formula $$CH_2=C(R°)CH_{3-m}X_m$$

including those having alkallyl groups such as:

$$CH_2=C(C_nH_{2n+1})CH<$$

and $$CH_2=C(C_nH_{2n+1})CH_2—,$$

wherein R° is a monovalent hydrocarbon group are reacted with organohydrosiloxanes under hydrosilation reaction conditions to form useful organofunctional polysiloxanes. The functional groups represented by X include a hydrocarbonoxy group, a cyanohydrocarbonoxy group, an acyloxy group, a halogen atom, a hydroxy group, a cyano group or a group having the formula —OC(O)NR$_2$ wherein R is a monovalent nitrogen-free organic radical, a divalent hydrocarbon group or hydrogen and may be the same or different throughout the same group or molecule, n is an integer of 1 to 18, m is an integer of 1 and when X is hydrocarbonoxy or acyloxy, m is 1 or 2. The very low degree (if any) of isomerization of the $CH_2=C(R°)CH_{3-m}$ group to unreactive species during the hydrosilation reaction results in high yields of the desired organofunctional polysiloxanes in the process of the present invention.

27 Claims, No Drawings

PROCESS FOR THE PREPARATION OF NOVEL ORGANOSILICON COMPOUNDS

BACKGROUND OF THE INVENTION

1. Field of the Invention

The invention relates to a novel process for producing organofunctional polysiloxanes in high yields by the addition reaction of an allyl compound and an organohydrosiloxane and relates to novel compositions comprising novel organofunctional polysiloxanes.

2. Description of the Prior Art

Certain types of organofunctional polysiloxanes are known in the prior art and are readily available as articles of commerce. The known organofunctional polysiloxanes are made by the reaction of poly(dimethylsiloxanes) containing SiH groups (organohydrosiloxanes) with olefinic compounds wherein the olefinic sites are allyl groups. The general reaction whereby the novel organofunctional siloxanes are created is:

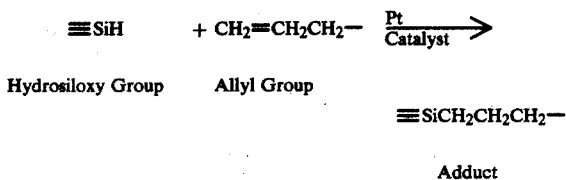

However, the above reaction is not the sole reaction that occurs during the preparation of the adduct. It has been established that a significant percentage of the allyl groups are isomerized under the addition reaction conditions to propenyl groups. The latter react very slowly, if at all, with the siloxane hydrogen atoms of the hydrosiloxane reactant. The isomerization and failure of the propenyl group to react can be depicted by the following formula:

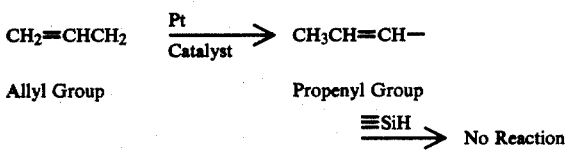

It has become accepted practice within the industry to use stoichiometric excesses (20 mole % or more) of the allyl group to insure complete reaction of all silanic hydrogen atoms. Another practice has been to scavenge the residual silanic hydrogen atoms with a reactant such as methanol or ethylene. The excess unreacted or isomerized allyl group if not removed can be present as diluent thereby reducing the potency or active concentration of the final material and most certainly requires separation procedures in order to secure a relatively concentrated or pure desired compound.

There is no prior art known regarding hydrosilation reactions of methallyl acetate or any other methallyl ester with hydrosilanes or hydrosiloxanes. The unobvious nature of the unexpectedly high yields obtained from reactions of methallyl acetate with hydrosiloxanes is accented by the low yields of corresponding products obtained from allyl acetate, isopropenyl acetate, or vinyl acetate. Both allyl acetate and isopropenyl acetate generate significant amounts of propylene (see J. Am. Chem. Soc., 79 974 (1957) in reactions with hydrosilanes or hydrosiloxanes. Vinyl acetate is reported to give a low yield of hydrosilation product in reaction with MD'M (U.S. Pat. Nos. 2,967,876 and 2,970,150). Methallyl acetate unexpectedly generates much higher yields of hydrosilation products with correspondingly lower yields of undesired by-products.

A foreign patent, Ger. Offen. No. 1,961,501 (see Chem. Abstract, 73, 78069f (1970)) to Shin Etsu of Japan, discloses that siloxanes containing polyether groups bonded to the siloxane by $\equiv SiCH_2CH(CH_3)CH_2O_2CR$ linkages can be made by reacting chloroisobutylsilicones with sodium polyether carboxylates. That process is inferior to that of this invention due to low yields, salt formation and by-products. The process of this invention provides for high yields of novel compositions $\equiv SiCH_2CH(R^\circ)CH_2O_2CR$ groups where R is hydrogen or a monovalent carbon-containing substituent other than polyether, e.g., monovalent hydrocarbon.

Also, U.S. Pat. No. 3,258,477 (Example 14) discloses the addition reaction of methallyl methacrylate and triethoxysilane or tribenzoyloxysilane. No prior art is known which teaches or suggests the addition reaction of any methallyl ester or similar ester with a hydrosiloxane.

British Pat. No. 1,077,664 discloses the reaction product of $MD_9D_9'M$ (a polyhydrosiloxane fluid in which M is $Me_3SiO_{0.5}$, D is $-Me_2SiO-$, and D' is $-MeHSiO-$) and isopropenyl acetate to yield "substituted polysiloxanes used in preparing single-stage polyether urethan foams." Experiments have indicated that such a reaction would not yield products with significant amounts of $\equiv SiCH_2CH(CH_3)OAc$ groups.

The unexpected and unobvious features of this invention are also obtainable with unsaturated esters containing two ester groups on the same carbon atoms, e.g., methallylidene diacetate. There is no prior art known regarding the hydrosilation of methallylidene diacetate, or any other olefinically unsaturated diacylate, $CH_2=C(R^\circ)CH(O_2CR)_2$. Allylidene diacetate has been reacted with methyldiethoxysilane, according to J. Am. Chem. Soc., 79, 3073 (1957). Compositions made with methallylidene or similar diacylates, however, are novel and higher yields are obtained than with allylidene diacetate.

Reactions of methallyl chloride with methyldichlorosilane and ethyldichlorosilane are reported in Chem. Abstract 50, 13726e (1956). The reaction of methyldichlorosilane with allyl chloride using chloroplatinic acid catalyst is reported to give a 40 percent yield of chloropropylmethyldichlorosilane, while the corresponding methallyl chloride reaction yields 70 percent of chloroisobutylmethyldichlorosilane (see Chem. Abstract 54, 22328b (1960). Higher yields of expected products were reported for methallyl chloride over allyl chloride in reactions with trichlorosilane, methyldichlorosilane, and dimethylchlorosilane in J. Am. Chem. Soc., 82, 3601 (1960), and indicated for the same reaction with deuterotrichlorosilane ($Cl_3SiD$) in J. Am. Chem. Soc., 86, 895 (1964) (see also U.S. Pat. No. 3,686,253). The reaction of methallyl chloride with diethylmethylsilane gives 45 percent of chloroisobutyldiethylmethylsilane according to Chem. Abstracts 55, 15331c (1961). The preparation of siloxanes (as opposed to silanes) containing chloroisobutyl groups is disclosed in J. Am. Chem. Soc., 82, 3601 (1960).

There is, however, only a single reference known in the prior art which discloses reactions of hydrosiloxanes (as distinguished from hydrosilanes) with methallyl chloride. This reference, J. Org. Chem., 38, 838 (1973), discloses reactions of pentamethyldisiloxane (MM'), heptamethyltrisiloxane (MD'M), and tris(trimethylsiloxy)silane ($M_3T'$), with methallyl chloride with respective yields of 97 percent, 32 percent, and 14 percent of the desired hydrosilation products (i.e., the corresponding chloroisobutyl siloxanes).

While it is known that hydrosilanes give higher yields of hydrosilation products with methallyl chloride than with allyl chloride, there is no reason to assume the same relationship for reaction of hydrosiloxanes. With the exception of MM', the yields with methallyl chloride were quite low (32 percent for MD'M, 14 percent for $M_3T'$) in the only known published examples. In the process of this invention, the unsaturated halide is added to the hydrosiloxane and higher yields of the desired product are obtained. No prior art is known which teaches the production of high yields of chloroisobutylsiloxanes by the addition of methallyl chloride to the hydrosiloxane pursuant to this invention.

Certain siloxanes containing chloroisobutyl groups are known as mentioned above and as shown in German Offen. No. 1,961,501 (Chem. Abstract 73, 78069f (1970)) and U.S. Pat. No. 3,414,604, having been prepared by cohydrolysis of the products obtained from reactions of hydrosilanes and methallyl chloride and methylchlorosilanes. Such compositions do not include chloroisobutylheptamethylcyclotetrasiloxane, i.e., $D_3D'CH_2CH(CH_3)CH_2Cl$, which has also not been made prior to the instant invention by hydrosilation of methallyl chloride with heptamethylcyclotetrasiloxane ($D_3D'$). The composition $D_3D'CH_2CH(CH_3)CH_2Cl$ is novel and useful and can be made in good yields by the process of the present invention.

Methallyl carbamates and substituted methallyl carbamates also undergo hydrosilation reactions to give higher yields of desired products than do the corresponding allyl derivatives, according to the processes of the instant invention. The products are also novel compositions of matter and no prior art is known to teach or suggest them. U.S. Pat. No. 3,426,057 discloses the reaction of hydrosiloxanes with carbamates derived from allyl or methallyl alcohols and toluene diisocyanate. The preparation of both carbamates is given as examples of this patent and the hydrosilation examples include only the allyl carbamate, so that no comparison with the methallyl carbamate can be made. This invention is concerned only with O-methallyl carbamates which hydrosilate to give structures $\equiv SiCH_2CH(CH_3)CH_2O_2CN=$. U.S. Pat. No. 3,652,629 discloses hydrosilations of N-methallyl carbamates, which give rise to different structures, $\equiv SiCH_2CH(CH_3)CH_2NRCO_2-$, which clearly differ from the novel compositions of this invention.

Simple methallyl ethers also are employed pursuant to this invention in addition reaction with hydrosiloxanes. Typical of such simple methallyl ethers are methallyl methyl ether, methallyl phenyl ether, 3-methallyloxypropionitrile, and others, which when hydrosilated give rise to compounds containing $\equiv SiCH_2CH(CH_3)CH_2OR$ groups where R is a carbon-containing substituent. According to this invention, simple methallyl ethers unexpectedly give higher yields of desired products in hydrosilation reactions than do the corresponding allyl ethers. Allyl ethers, such as those shown in U.S. Pat. No. 3,794,673, under conditions typical to hydrosilation reactions, undergo significant rearrangement to propenyl ethers which are unreactive toward hydrosilation. Methallyl ethers have been found unexpectedly to have a much lower propensity toward isomerization to relatively unreactive 2-methylpropenyl ethers, and accordingly give higher yields in hydrosilation reactions with hydrosiloxanes. Similarly, methacrolein acetals have unexpectedly been found to give higher yields than acrolein acetals and are included as a reactant in this invention. Acetals of methacrolein can be considered as methallyl ethers with two alkoxide groups on the same carbon atom. Reactions of acrolein acetals with hydrosiloxanes are disclosed in J. Org. Chem., 35, 4180 (1970).

Methacrolein-pentaerythritol condensates are disclosed in U.S. Pat. Nos. 3,381,019 and 3,513,183. The sulfate salts of the addition reaction products of these condensates and hydrosiloxanes are also disclosed in the patents which, however, fail to disclose or suggest the compositions of this invention or the methods of this invention and there is no suggestion that methacrolein-pentaerythritol is a preferred reactant or provides the advantages secured by this invention.

By way of prior art, U.S. Pat. Nos. 3,716,517 and 3,716,518 disclose hydrosilations of methallyl ethers containing two or more units derived from ethylene oxide or propylene oxide. These reactions involve hydrosilanes (as differentiated from hydrosiloxanes) and use peroxide catalysts instead of platinum catalysts used in processes of the instant invention. U.S. Pat. No. 3,258,477 shows a structure, $(CH_3CO_2)_3SiCH_2CH(CH_3)CH_2O(CH_2CH_2O)_4COC(CH_3)=CH_2$, with no working example. The same structure appears in U.S. Pat. Nos. 3,398,210 and 3,567,497.

The processes and compositions of the present invention regarding reactions of simple methallyl ethers with hydrosiloxanes are not shown in the prior art.

Hydrosilation reactions of silyl ethers (i.e., $\equiv Si-OC\equiv$) of allyl or methallyl alcohols do appear in the prior art. For example, U.S. Pat. No. 2,898,361 discloses the respective reactions of the trimethylsilyl ethers, $(CH_3)_3SiOC\equiv$, of allyl or methallyl alcohols with tetramethyldisiloxane. There is no indication that a higher yield was obtained with the methallyl ether, and the primary examples used the allyl ether. It appears from this patent that the methallyl silyl ethers offer no advantage.

Similarly, U.S. Pat. No. 3,622,609 discloses the respective reactions of allyl or methallyl alcohols with dimethylchlorosilane to form the dimethylsilyl ethers. These, on treatment with platinum catalysts, form linear polymers, which hydrolyze and condense to form the same product claimed in U.S. Pat. No. 2,898,361 above. Again, no advantage for using methallyl over allyl was noted in the patent, although one should have been very apparent, if obtained. The latter two examples of prior art differ from the processes and products of the instant invention, which is not concerned with silyl ethers of methallyl alcohol.

There do not appear to be any reactions between hydrosiloxanes and methallyl cyanide disclosed in the prior art. Methallyl cyanide does react with hydrosiloxanes to provide higher yields than does allyl cyanide. U.S. Pat. Nos. 3,347,895 and 3,358,009 disclose gamma-cyano-gamma-methyl-butyl groups without specifying how, if at all, they are bonded to silicon and fail to disclose methallyl cyanide or any derivatives thereof. Both patents as well as U.S. Pat. No. 3,642,851 disclose the 3-cyanopropyl group but fail to disclose or suggest the methallyl derivatives disclosed and claimed herein.

No prior art is known to exist regarding reactions of methallyl alcohol with hydrosiloxanes which give higher yields than reactions of hydrosiloxanes and allyl alcohol. Compounds with $\equiv SiCH_2CH(CH_3)CH_2OH$ groups have been prepared by hydrosilation and subsequent hydrolysis of methallyl silyl ethers as shown by U.S. Pat. Nos. 2,898,361 and 3,622,009. The direct hydrosilation of methallyl alcohol is novel and patentable as are the resultant compositions. U.S. Pat. No. 2,888,454 discloses the thermal decomposition of $M_2D'(CH_2)_3OH$ by loss of $Me_3SiOH$ and formation of cyclic disiloxane derivative. The same reaction occurs with $M_2D'CH_2CH(CH_3)CH_2OH$, prepared in the instant invention, and at significantly lower temperatures.

Three different groups, V. F. Mironov and A. D. Petrov in Russia, J. W. Curry from Dow Corning, and K. Kojima in Japan, have published work on polymers prepared from unsaturated silanes, or from dihydrosilanes and diolefins. The Russian work in particular mentions polymerization of methallylsilanes and allylsilanes, with no advantage (e.g. the obtaining of higher molecular weight polymers) noted for methallylsilanes. The present invention is not concerned with methallylsilanes, but this prior art does confirm the unexpected nature of the present invention in the attainment of higher yields with methallyl compounds, since "dimethyl(2-methally)silane scarcely polymerizes at all", when treated with platinum catalyst (see Chem. Abstract, 54, 1271b (1960)) for abstract of Russian paper).

U.S. Pat. No. 3,632,715 discloses compounds containing $\equiv SiCH_2CH(CH_3)CH_2SH$ groups, with which the instant invention is not concerned. The prior art has failed to recognize, the unobvious and unexpected advantages to be gained from the use of methallyl compounds in addition reactions with hydrosiloxanes. Furthermore, allyl phenyl selenide is reported to give a higher yield of product in reaction with triethylsilane than does methallyl phenyl selenide (see Chem. Abstract, 84, 164921m (1976)) which would discourage the substitution of methallyl compounds for allyl compounds in reactions of this kind.

It is shown hereinbelow that the addition of hydrosiloxanes to organic compounds having the formula $$CH_2 = C(R^*)CH_{3-m}X_m$$

wherein X is a functional group and R° is a monovalent hydrocarbon group as more fully described hereinbelow instead of allylic compounds unexpectedly results in higher yields of more highly concentrated desired organofuncational polysiloxanes. Such higher yields are believed to be due to no, or only slight, isomerization of the group $$CH_2 = C(R^*)CH_{3-m}$$

to unreactive species during hydrosilation such as usually occurs in the case of the allylic compounds.

SUMMARY OF THE INVENTION

This invention is based in part on the novel and unexpected discovery that compounds of the formula $$CH_2 = C(R^*)CH_{3-m}X_m$$

including those having alkallyl groups such as:

$$CH_2 = C(C_nH_{2n+1})CH<$$

and $$CH_2 = C(C_nH_{2n+1})CH_2-,$$

undergo hydrosilation reactions with $\equiv SiH$ groups of hydropolysiloxanes in much cleaner fashion and in higher yields than do allyl groups. Since the reaction of silanic hydrogen and the alkallyl group is cleaner, higher yields of the desired polysiloxane in more concentrated form can be obtained with less excess olefinic reactant, therefore, resulting in higher yields of the desired organofunctional polysiloxane. This invention thus provides novel processes whereby improved organofunctional polysiloxanes are prepared, with inherently lower excess of the unsaturated allyl compound being a keypoint in such processes. The novel organofunctional polysiloxanes provided by this invention are further characterized as having organofunctional groups bonded to silicon by carbon to silicon linkages.

Inherent in obtaining high yields from reactions of certain methallyl compounds with hydrosiloxanes in the instant invention is the order of combination of reactants. When applicable, higher yields are obtained when the methallyl compound is added incrementally to the reactive hydrosiloxane. In the case of methallyl chloride, this is a critical factor in obtaining high yields. While the order of combination of reactants may not seem important, its discovered importance as part of the instant invention is completely unobvious and unexpected, based on the prior art teachings. In general, prior art reactions were performed by initially totally combining all reactants, followed by addition of the platinum catalyst. In some instances of the prior art the hydrosiloxane was added incrementally to specific olefinic reactants with which a catalyst was mixed.

More particularly, the novel and unexpected discovery of the low degree of isomerization of compounds having the preferred alkallyl groups during hydrosilation permits the preparation of higher yields and more concentrated organofunctional polysiloxane. These materials are novel compositions of matter having properties not attainable by prior art methods.

The unique compounds produced by the process of the invention may be employed for a plurality of different uses, including use as intermediates for purposes of introducing a particular organic group into siloxane polymers by conventional equilibration techniques. In addition, they find direct use as low to intermediate viscosity oils for the same general purposes as conventional silicone oils, and for such special applications as their specific functional group might indicate. Thus, such general uses would include application as mold releases, cosmetic ingredients, lubricants, antifoams, hydraulic fluids, etc., whereas the specific uses would depend on utilization of polar groups, for example, for greater lubricity, solvent resistance, and the like.

In particular, certain of the novel compounds herein described, can be used as surfactants or foam stabilizers in the preparation of various types of urethane foams, including flexible, rigid, high resiliency, polyester, semiflexible, mechanically frothed, or microcellular urethane foams. Others of the novel organofunctional polysiloxanes of the present invention also can be used in water systems as wetting agents, thickeners, and emulsifiers. They are particularly suited for incorporation in aerosol shaving cream formulations. Certain of these novel materials are useful as textile fiber lubricants, lubricants in other fields and as additives or intermediates for forming lubricants.

DETAILED DESCRIPTION OF THE INVENTION

The organofunctional polysiloxanes of this invention are adducts of an organohydrosiloxane and an organic functional compound having a $CH_2=C(R°)CH_2-$ or a $CH_2=C(R°)CH<$ group, hereinafter called alkallyl groups, wherein R° is a monovalent hydrocarbon, said compound preferably being composed of carbon and hydrogen and one or more of oxygen, nitrogen and halogen. Isomerization of the $CH_2=C(R°)CH_2-$ and $CH_2=C(R°)CH<$ groups pursuant to the present invention occurs not at all or to a slight degree under hydrosilation conditions, but, when it does occur, it is much less than with corresponding allyl type compounds. When it does occur, to insure complete reaction between the organic functional compounds, hereinafter also called alkallyl compounds, and organohydrosiloxanes of the present invention, a slight excess of alkallyl should therefore be used. The precise molar ratio of $CH_2=C(R°)CH_2-$ or $CH_2=C(R°)CH<$ groups to silanic bonded hydrogen is not narrowly critical. A molar ratio in the range of 0.85 to 1.3 is effective. As the molar ratio is increased above 1:1, the processes of the present invention become less economical. Also, the excess unreacted organic functional compound acts as a diluent, thereby reducing the potency or active concentration of the final product. Similarly, at ratios below 1:1, the unreacted organohydrosiloxane acts as a diluent.

The organohydrosiloxane reactant of the present invention can be a monohydrosiloxane, a dihydrosiloxane or a polyhydrosiloxane wherein any valences of silicon not bonded to hydrogen or to oxygen in a silicon to oxygen to silicon bond are bonded to a monovalent hydrocarbon group (such as those given above for R°) or a monovalent halohydrocarbon group (such as chloroethyl, chlorophenyl, chlorobenzyl, etc.). The substituents (other than hydrogen) on silicon should not interfere with the hydrosilation reaction. The preferred substituent on silicon is the methyl group. Other groups such as chloropropyl, phenylethyl, or chloroisobutyl are illustrative of functional groups which may be used as substituents on silicon to improve or modify the performance of the final product. The hydrosiloxane molecules may vary in molecular weight in the hydrosiloxane reactant. Cyclic organohydrosiloxanes wherein hydrogen is attached to a silicon atom which either forms part of the ring or which does not form part of the ring can also be used as the organohydrosiloxane reactant in the present invention. Suitable organohydrosiloxane reactants include those having one or more unit of the formula: $HR'_aSiO_{3-a/2}$ and one or more units of the formula: $R'_bSiO_{4-b/2}$ wherein R' is a monovalent hydrocarbon group or a halogen-substituted monovalent hydrocarbon group as described hereinabove, a is an integer of 0 to 2, preferably 1, and b is an integer of 0 to 3, preferably 2. R' preferably contains 1 to 18 carbon atoms.

The monohydrosiloxane structures include, but are not limited to:

$(CH_3)_3SiOSi(CH_3)_2H$

-continued

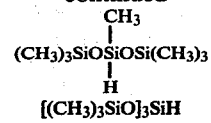

$[(CH_3)_3SiO]_3SiH$

$[(CH_3)_3SiO]_3SiOSi(CH_3)_2H$

The dihydrosiloxanes of the present invention may have structures wherein the two hydrogen atoms are attached to the same silicon atom or to different silicon atoms of the molecule. Also, the hydrogen atoms may be located either terminally or internally in each molecule. Typical examples of dihydrosiloxanes include the following, but are not limited thereto:

$$\begin{array}{c}CH_3\\|\\(CH_3)_3SiOSiOSi(CH_3)_3\\|\\OSi(CH_3)H_2\end{array} \quad O[(CH_3)_2SiO]_3Si(CH_3)OSi(CH_3)H_2$$

The dihydrosiloxanes most preferred in the present invention specifically include those structures so designed as to have two $\equiv SiH$ groups in each molecule, i.e., the two hydrogen atoms are attached to different silicon atoms of the dihydrosiloxane molecule. However, the molecules may vary widely in molecular weight and in structure from each other.

The polyhydrosiloxanes may also have any of several structures including blends thereof; such structural types as the following are included but are not inclusive of all the structures operative in the present invention.

| | |
|---|---|
| $(CH_3)_3SiO[(CH_3)_2SiO]_x[(CH_3)SiHO]_ySi(CH_3)_3$ | where $x=0-300$ $y=3-30$ |
| $H(CH_3)_2SiO[(CH_3)_2SiO]_x[(CH_3)SiHO]_ySi(CH_3)_2H$ | where $x=0-300$ $y=1-30$ |
| $CH_3Si([(CH_3)_2SiO]_xOSi(CH_3)_2H)_3$ | where $x=0-100$ |
| $CH_3Si([(CH_3)_2SiO]_x[(CH_3)SiHO]_yOSi(CH_3)_3)_3$ | where $x=0-100$ $y=1-30$ |
| $CH_3Si([CH_3)_2SiO]_x[(CH_3)SiHO]_yOSi(CH_3)_2H)_3$ | where $x=0-100$ $y=0-10$ |
| $HR'_2SiO[R'_2SiO]_xSiR'_2H$ | where $x=0-300$ |

The organohydrosiloxane reactant may thus have a wide variety of structures, meaning that the operation of the processes of this invention is not severely limited by the structure of either reactant, except that the hydrosiloxane molecule must contain at least one reactive $\equiv SiH$ group, and the alkallyl reactant molecule must contain at least one reactive alkallyl group.

The organohydrosiloxanes are reacted with the alkallyl reactant according to the present invention at addition reaction conditions under which the silicon-bonded hydrogen and the silicon to which it is bonded become bonded respectively to the vicinal carbon atoms comprising the unsaturation of the $CH_2=C(R°)CH_2-$ or $CH_2=C(R°)CH<$ groups of the organic functional compound.

The organic functional reactant used in this invention has the formula:

$$CH_2=C(R°)CH_{3-m}X_m$$

wherein R° is a monovalent hydrocarbon group and preferably is an alkyl group, $-C_nH_{2n+1}-$, X is a hydrocarbonoxy group, a cyanohydrocarbonoxy group, an acyloxy group, a halogen atom, a hydroxy group, a cyano group or a group having the formula $-OC(O)NR_2$ wherein R is a monovalent nitrogen-free organic radical, a divalent hydrocarbon group, or hydrogen and may be the same or different throughout the same group or molecule, n is an integer of 1 to 18, m is an integer of 1 and when X is hydrocarbonoxy or acyloxy, m is 1 or 2. Each of R°, R and X, when it is hydrocarbonoxy, cyanohydrocarbonoxy or acyloxy, preferably contains 1 to 18 carbon atoms. Typical hydrocarbonoxy groups are methoxy, ethoxy, butoxy, stearoxy, phenoxy, phenethoxy, and the like. Representative cyanohydrocarbonoxy groups are cyanomethoxy, beta-cyanoethoxy, delta-cyanobutoxy, 18-cyanostearoxy, p-cyanophenoxy and the like. Typical acyloxy groups include acetoxy, butyryloxy, caproyloxy, stearoyloxy, phenylacetyloxy, phenylbutyryloxy, benzoyloxy, biphenylcarbonyloxy, cinnamoyloxy, acryloyloxy, methacrylyloxy, and the like. Typical halogen atoms include chlorine, fluorine, iodine and bromine. Typical monovalent nitrogen-free organic radicals represented by R include the monovalent hydrocarbon groups which are preferred including those typified above and the divalent hydrocarbon group represented by R include alkylene groups preferably having 2 to 18 carbon atoms, e.g., 1,2-ethylene, 1,3-propylene, 1,2-propylene, 1,18-octadecylene and the like and arylene groups having 6 to 18 carbon atoms such as phenylene, o, p or m-phenylene dimethylene, phenylethylene, naphthylene and the like. Preferred organic functional compounds are those composed of carbon, hydrogen, and oxygen and/or halogen and/or nitrogen and especially preferred are the methallyl compounds where R° is methyl. Illustrations of useful organic functional reactants include but are not limited to the following compounds:

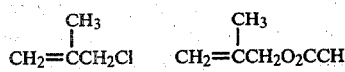
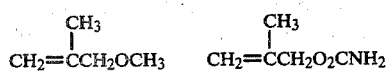
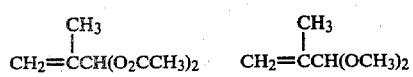
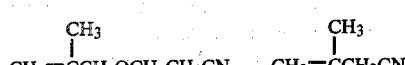
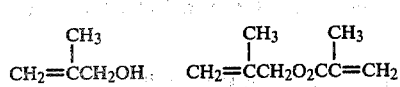

-continued

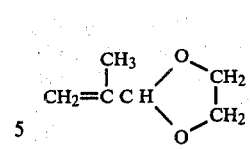

Reaction conditions are not narrowly critical. The reaction temperature should be elevated and may be from 50° to 150° C. for example, with 80°–120° C. preferred. The use of a nonreactive solvent for the reactants such as toluene is preferred. However, it is not an absolute requirement because certain reactions can be run in the absence of solvent without changing reaction conditions or equipment. A cosolvent is required for reactions where the organohydrosilanes and the organic functional compound form very high viscosity products. The reaction between the organohydrosiloxanes and the organic functional compound are conveniently catalyzed by platinum-containing hydrosilation catalysts which are in commercial use or known to be useful by those skilled in the art. For example, chloroplatinic acid hexahydrate dissolved in 1,2-dimethoxyethane or in isopropanol is an effective catalyst. A reduced platinum catalyst of the type described in U.S. Pat. No. 3,220,972 is also suitable. Platinum metal, heterogeneously deposited on charcoal, has been found to be the preferred catalyst for the co-reactions of hydrosiloxanes and certain substituted allyl compounds. Catalyst concentrations similar to those used in the prior art are useful. For example, as disclosed in U.S. Pat. No. 3,507,815, useful catalysts may contain from 0.001 to 5.0 weight percent platinum based on the weight of the reactants. In regard to the solvent and catalyst considerations expressed above, the processes of the present invention are not narrowly critical with regard to temperature, solvent, or catalyst, and are not thereby limited.

The processes of the present invention are operable in many versions of standard reaction equipment which have provisions for adequate heating, cooling, agitation, and maintenance of an inert atmosphere. The reaction scale is not limited by size and may range from several grams to several thousand kilograms. Thus, these processes are not narrowly critical with regard to scale or equipment used.

In the present invention it is in many cases advantageous to prepare the organofunctional siloxane by adding the organic functional compound, $CH_2=C(R°)CH_{3-m}X_m$, to the organohydrosiloxane. For example, the organofunctional siloxane, e.g., $D_3D'CH_2CH(CH_3)CH_2Cl$ is preferably prepared by adding methallyl chloride to the reactive $D_3D'$ which is at temperature and contains platinum catalyst. The reaction can be depicted as follows:

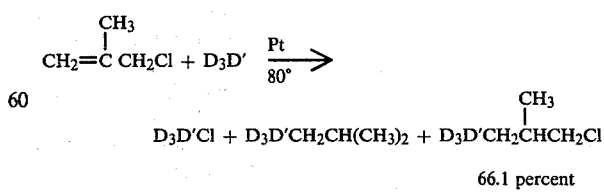

66.1 percent

The ensuing reaction results in a 66.1 percent distilled yield of the desired product. If methallyl chloride and $D_3D'$ are combined prior to heating and adding the catalyst, the yield of $D_3D'$ $CH_2CH(CH_3)CH_2Cl$ is lowered to 60 percent, and $D_3D'$ $CH_2C(CH_3) = CH_2$ also appears as a product. If $D_3D'$ is added to reactive methallyl chloride, $D_3D'Cl$ becomes the major product, with a very low yield of the desired $D_3D'$ $CH_2CH(CH_3)CH_2Cl$. This illustrates an instance wherein considerably higher yields are secured by adding the organic functional compound to the organohydrosiloxane.

By comparison, if allyl chloride is added to $D_3D'$ under the same conditions, one gets only a 19.4 percent yield of $D_3D'(CH_2)_3Cl$. The reaction is depicted by the equation:

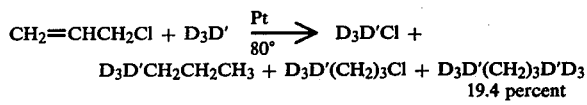

When allyl chloride and $D_3D'$ are combined at the start, the yield of $D_3D'(CH_2)_3Cl$ drops to 11.2 percent.

Thus, the yield for the $D_3D'$-methallyl chloride reaction, according to the process of the present invention, is 66.1 percent (more or less), while that for the $D_3D'$-allyl chloride reaction is 19.4 percent (more or less). Clearly, there is a large advantage to be gained in using methallyl chloride over allyl chloride, with a further advantage to be gained by adding the methallyl chloride to reactive $D_3D'$ as opposed to other modes of combining the reactants.

Similarly, the addition of MD'M to reactive methallyl chloride yields 34 percent of $M_2D'CH_2CH(CH_3)CH_2Cl$. When the reactants were combined at the start of the reaction, a similar low yield was obtained. When the reaction was run according to one preferred process of the instant invention, namely by adding methallyl chloride to reactive MD'M, the yield of $M_2D'CH_2CH(CH_3)CH_2Cl$ was improved to 50.2 percent, as depicted by the following equation:

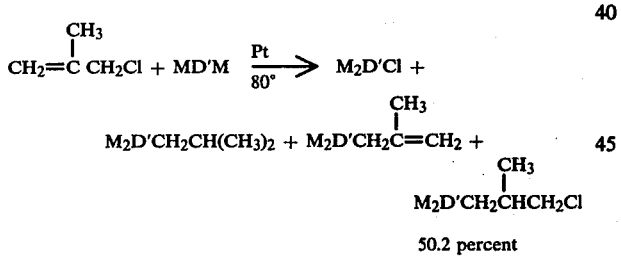

Corresponding reductions in yields of the other undesired products were obtained. This represents a substantial improvement in the preparation of $M_2D'CH_2CH(CH_3)CH_2Cl$ either by reacting MD'M with methallyl chloride, or by cohydrolysis of $MeSiCl_2CH_2CH(CH_3)CH_2Cl$ with excess $Me_3SiCl$.

The fact that the high yield of $D_3D'CH_2CH(CH_3)CH_2Cl$, i.e., chloroalkylsiloxane, is specific to compounds of the formula $CH_2 = C(R°)CH_{3-m}X_m$, e.g., methallyl chloride, is demonstrated by several other reactions of different chloroolefins with $D_3D'$. For example, the reaction of $D_3D'$ with the isomeric $CH_2 = CHCHClCH_3$ is depicted by the equation:

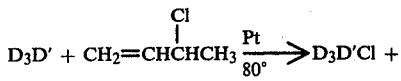

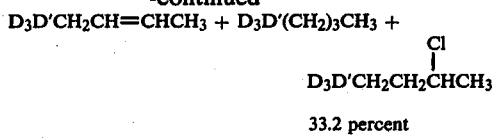

33.2 percent

In this case the $CH_2 = CHCHClCH_3$ was added to reactive $D_3D'$ and yielded only 33.2 percent of the desired hydrosilation product. A number of other different olefinic chlorides were reacted with $D_3D'$ as follows and none gave higher yields of the desired hydrosilation product than the $CH_2 = C(R°)CH_{2-m}X_m$ compound:

$CH_2 = CCl_2$ to $D_3D'CH_2CHCl_2$
$CH_2 = C(CH_2Cl)_2$ to $D_3D'CH_2CH(CH_2Cl)_2$
$CH_2 = CClCH_2Cl$ to $D_3D'CH_2CHClCH_2Cl$
$CH_2 = CHCHClCH_2Cl$ to $D_3D'CH_2CH_2CHClCH_2Cl$
$(CH_3)_2C = CHCl$ to $D_3D'C(CH_3)_2CH_2Cl$.

Hydrosilations of $CH_2 = C(R°)CH_2OOCR$ compounds, such as methallyl esters provides viable high yields of ester-functional silicones not similarly accessible via hydrosilations of vinyl esters, allyl esters, or isopropenyl esters. Reactions of the respective acetates with $D_3D'$ were performed and are depicted by the following equations:

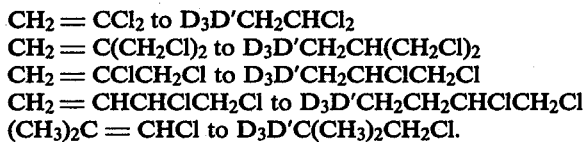

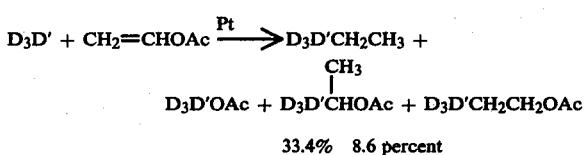

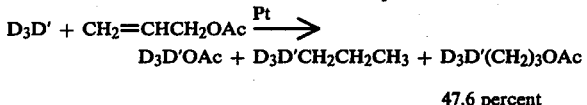

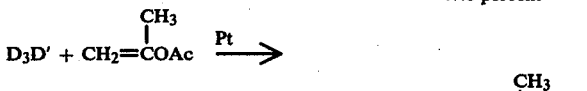

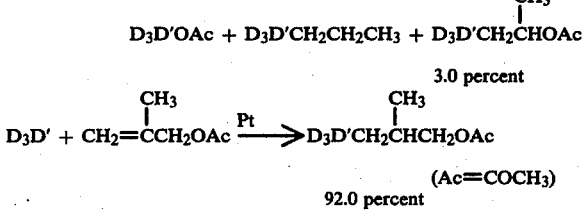

As can be seen from these equations, vinyl acetate reacted with $D_3D'$ to give a combined 42.0 percent yield of two hydrosilation products (alpha/beta isomers, 4/1 ratio), while allyl acetate yielded 47.6 percent of $D_3D'(CH_2)_3OAc$. Isopropenyl acetate produced only 3.0 percent of the desired hydrosilation product, while methallyl acetate yielded 92.0 percent of the desired product. Thus, the yield with the compound of the formula $CH_2 = C(R°)CH_{3-m}X_m$, that is methallyl acetate, in reactions with $D_3D'$, was about double the best obtained with other olefinic acetates.

The results were similar when MD'M was used in place of $D_3D'$ as depicted by the following equations:

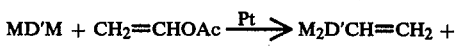

-continued $$M_2D'CH_2CH_3 + M_2D'OAc\ M_2D'CHOAc\ (10\ percent) + \\ M_2D'CH_2CH_2OAc\ (24\ percent) + M_2D'(CH_2)_2D'M_2$$

$$MD'M + CH_2=\overset{\overset{CH_3}{|}}{C}CH_2OAc \xrightarrow{Pt}$$

$$M_3T' + M_2T'OAc + M_2D'CH_2\overset{\overset{CH_3}{|}}{C}HCH_2OAc$$
67.2 percent The $M_2D'CH_2CH(CH_3)CH_2OAc$ yield is about double that of the combined vinyl acetate hydrosilation products. An older example for the reaction of MD'M and vinyl acetate appears in U.S. Pat. Nos. 2,970,150 and 2,967,876 with an asserted 25.6 percent yield of the desired hydrosilation product. Although both patents indicate a higher weight yield, the product obviously contains materials other than the desired product.

British Pat. No. 1,077,664 claims the reaction product of $MD_9D'_9M$ hydrosiloxane fluid and isopropenyl acetate to yield "substituted polysiloxanes used in preparing single-stage polyether urethan foams." It is obvious from the above-described tests that such a reaction would not yield products with significant amounts of $\equiv SiCH_2CH(CH_3)OAc$ groups. From the results obtained in this invention any methallyl ester can be expected to give a high yield of hydrosilation product. Thus, methallyl stearate can be prepared from methallyl alcohol and stearic acid, and reacted with a polyhydrosiloxane to yield a stearate-functional silicone with potential utility as a fiber lubricant, for example.

Another substituted allyl ester, $CH_2 = C(R°)CH_2\text{-}OOCR$, e.g., methallyl ester, of great potential utility in the silicones area is methallyl methacrylate. This diolefinic ester can be reacted pursuant to this invention with $D_3D'$ or polyhydrosiloxanes to give methacrylate-functional silicones of interest in photocured coatings. Methallyl acrylate can be reacted pursuant to this invention to produce acrylate functional silicones potentially useful in photocured coatings. Methacrylatefunctional silicones are useful as disclosed in a Russian article (Chem. Abstract 85, 96104r (1976)).

The reaction of $D_3D'$ with methallyl methacrylate has been carried out according to the following equation:

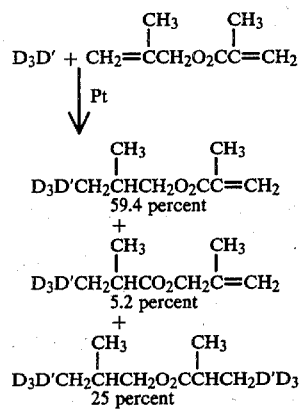

The test revealed a high yield of the desired hydrosilation products for methallyl methacrylate with no cleavage products. The reaction was run at 1:1 stoichiometry to emphasize side reactions. If an excess of methallyl methacrylate had been used, the yield of $D_3D'CH_2(CH(CH_3)CH_2O_2CC(CH_3) = CH_2$ would have been higher.

Higher yields of silicone diacylates are also obtained when $D_3D'$ is reacted with substituted allylidene diacylates, $CH_2 = C(R°)CH(OOCR°)_2$, e.g., methallylidene diacetate than with the unsubstituted allylidene diacylates, e.g., allylidene diacetate.

$$D_3D' + CH_2=CHCH(OAc)_2 \xrightarrow{Pt}$$
$$D_3D'OAc + D_3D'\overset{\overset{OAc}{|}}{C}HCH_2CH_3 + \\ D_3D'CH_2CH_2CH(OAc)_2$$
49.1 percent $$D_3D' + CH_2=\overset{\overset{CH_3}{|}}{C}CH(OAc)_2 \xrightarrow{Pt} D_3D'CH_2\overset{\overset{CH_3}{|}}{C}HCH(OAc)_2$$
93.5 percent A similar relationship holds for reactions of MD'M with the respective methallylidene and allylidene diacetates as shown by the equations:

$$MD'M + CH_2=CHCH(OAc)_2 \xrightarrow{Pt}$$
$$CH_3CH=CHOAc + M_2D'OAc + \\ M_2D'CH_2CH=CHOAc + M_2D'CH_2CH_2CH(OAc)_2$$
39 percent $$MD'M + CH_2=\overset{\overset{CH_3}{|}}{C}CH(OAc)_2 \xrightarrow{Pt} M_2D'CH_2\overset{\overset{CH_3}{|}}{C}HCH(OAc)_2$$
80 percent In both reactions of methallylidene diacetate, only trace amounts of the corresponding acetoxysiloxanes ($D_3D'OAc$, $M_2D'OAc$), plus $(CH_3)_2C = CHOAc$, were obtained.

Thus, it is obvious that the use of methallylidene diacetate as compared to allylidene diacetate gives much higher yields of hydrosilation products, and that methallyl acetate gives higher yields than allyl acetate. In addition to $D_3D'CH_2CH(CH_3)CH_2OAc$, $M_2D'CH_2CH(CH_3)CH_2OAc$, and $D_3D'CH_2CH(CH_3)CH_2O_2C(CH_3) = CH_2$, the compositions of $D_3D'CH_2CH(CH_3)CH(OAc)_2$, $M_2D'CH_2CH(CH_3)CH(OAc)_2$, $D_3D'CH(OAc)CH_2CH_3$, and $M_2D'CH_2CH=CHOAc$ mentioned hereinabove are novel compositions of matter.

Simple substituted allyl ethers, $CH_2=C(R°)\text{-}CHOR°$ and $CH_2 = C(R°)CHORCN$ (wherein R is a divalent hydrocarbon group), e.g., methallyl ethers, give higher yields of the desired product in reactions with organohydrosiloxanes than do the corresponding allyl ethers. When the methyl allyl and methallyl ethers and cyanoethyl allyl and methallyl ethers were compared in reactions with $D_3D'$, the methallyl versions gave higher yields in both cases as depicted by the following equations:

$$D_3D' + CH_2=CHCH_2OCH_3 \xrightarrow{Pt}$$
$$D_3D'(CH_2)_3OCH_3,\ 55\ \text{percent}$$

$$D_3D' + CH_2=\overset{\overset{CH_3}{|}}{C}CH_2OCH_3 \xrightarrow{Pt}$$
$$D_3D'CH_2\overset{\overset{CH_3}{|}}{C}HCH_2OCH_3\ 91\ \text{percent}$$

$$D_3D' + CH_2=CHCH_2OCH_2CH_2CN \xrightarrow{Pt}$$

-continued

D₃D'(CH₂)₃OCH₂CH₂CN, 80 percent

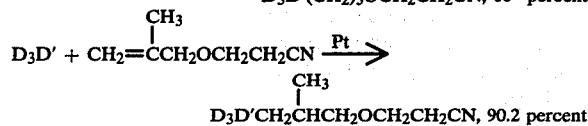

D₃D'CH₂CHCH₂OCH₂CH₂CN, 90.2 percent

Without being bound to theory, the higher yields of methallyl ethers are attributed to the fact that allyl ethers isomerize to unreactive propenyl ethers under hydrosilation conditions, while the corresponding isomerization of methallyl ethers occurs to a very limited extent, if at all. The hydrosilation products of the methallyl ethers, i.e., D₃D'CH₂CH(CH₃)CH₂OCH₃, and D₃D'CH₂CH(CH₃)CH₂OCH₂CH₂CN are novel compositions of matter.

When D₃D' was reacted with a mixture of methallyl cyanide CH₂ = C(CH₃)CH₂CN, and its isomer, senecionitrile (CH₃)₂C = CHCN, an almost quantitative conversion of methallyl cyanide to D₃D'CH₂CH(CH₃)CH₂CN occurred. The senecionitrile was recovered unchanged. The corresponding D₃D'-allyl cyanide reaction (Example 14) gave a 86.7 percent yield of a mixture of hydrosilation products, consisting mainly of D₃D'(CH₂)₃CN, but apparently containing isomeric products D₃D'CH(CH₃)CH₂CN, and D₃D'(CN)CH₂CH₃. The presence of isomeric products limits the commercial utility of the latter mixture.

Comparative reactions between D₃D' and a substituted allyl alcohol, CH₂ = C(R°)CH₂OH, e.g., methallyl alcohol, and D₃D' and allyl alcohol as depicted by the equations:

D₃D' + CH₂=CHCH₂OH $\xrightarrow{Pt}$ D₃D'OCH₂CH₂CH₃ + D₃D'(CH₂)₃OH + D₃D'(CH₂)₃OD'D₃
71 percent

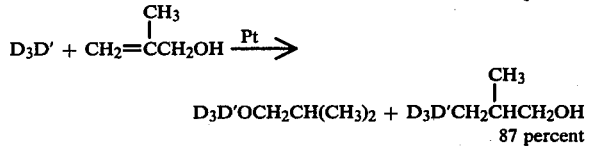

D₃D'OCH₂CH(CH₃)₂ + D₃D'CH₂CHCH₂OH
87 percent have shown that a higher yield and cleaner reaction was obtained with methallyl alcohol. The MD'M-methallyl alcohol reaction (Example 18) which gave a higher yield of M₂D'CH₂CH(CH₃)CH₂OH was complicated by thermal decomposition of that product during workup.

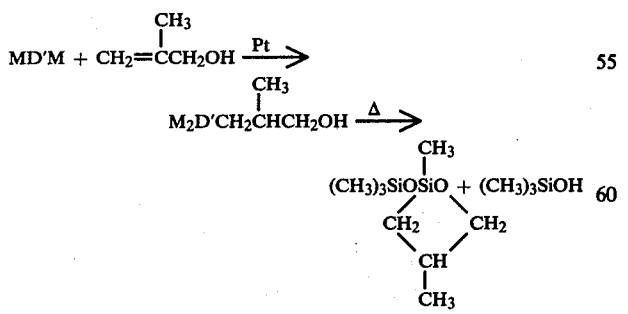

A similar decomposition, at much higher temperature, is reported for the MD'M - allyl alcohol adduct in U.S. Pat. No. 2,888,454. Both D₃D'CH₂CH(CH₃)CH₂OH and M₂D'CH₂CH(CH₃)CH₂OH are new compositions of matter, as is the cyclic decomposition product of the latter.

In all reactions carried out with the substituted allyl compounds, CH₂ = C(R°)CH₃₋ₘXₘ, according to this invention, it was found that the silicon-bonded hydrogen atom of the organohydrosiloxane attached to the internal carbon atom of the olefinically unsaturated group, CH₂ = C(R°)-, i.e., the carbon atom to which the R° group is bonded, rather than the terminal carbon atom of the group, and the silicon atom, to which said hydrogen atom was bonded, attached to the external carbon atom of said olefinically unsaturated group rather than said internal carbon atom, and thus resulted in a ≡SiCH₂C(R°)- linkage.

In one broad embodiment the novel reaction products are organofunctional siloxanes having at least one unit of the formula:

$$[(Y_mCH_{3-m}CH(R°)CH_2)]_aR_b'SiO_{\frac{4-a-b}{2}}$$

wherein a is an integer of 1 to 3, preferably 1, b is an integer of 0 to 2, preferably 1 or 2, a+b is an integer of 1 to 3, preferably 2 to 3, m is an integer of 1 to 2, when m is 1, Y is a hydrocarbonoxy group, a cyanohydrocarbonoxy group, a cyano group, an acyloxy group or a group having the formula —OC(O)NR₂ wherein R is a monovalent nitrogen-free organic radical or hydrogen and may be the same or different throughout the same group or molecule, R° is a monovalent hydrocarbon group, and when m is 2, Y is hydrocarbonoxy or acyloxy, and R is hydrogen or a monovalent hydrocarbon group and may be the same or different throughout the same group or molecule.

The organofunctional siloxane product can also contain one or more unit of the formula:

$$R_c'SiO_{\frac{4-c}{2}}$$

wherein c is an integer of 0 to 3, preferably 2 to 3, and R' is as defined hereinabove. Thus, preferred organofunctional siloxanes of this invention have the formula:

$$\left[(Y_mCH_{3-m}CH(C_nH_{2n+1})CH_2)_aR_b'SiO_{\frac{4-a-b}{2}}\right]_w\left[R_c'SiO_{\frac{4-c}{2}}\right]_z$$

wherein Y, m, a, b and R' are as defined hereinabove, n is an integer of 1 to 18, w is an integer of at least 1, preferably 1 to 100, and z is an integer of at least 0, preferably 1 to 300.

Particularly preferred organofunctional siloxanes of this invention have the formula:

$$[(XCH_2CH(C_nH_{2n+1})CH_2)_xR_{2-x}SiO]_y[R_2SiO]_{4-y}$$

wherein X is a hydrocarbonoxy group, a cyanohydrocarbonoxy group, an acyloxy group, a halogen atom, a hydroxy group, a cyano group or a group having the formula: —OC(O)NR₂ wherein R is a monovalent nitrogen-free organic radical and may be the same or different in the same molecule, n is an integer of 1 to 18, x is an integer of 1 or 2 and y is an integer of 1 to 4.

Because of the wide variety of structures which can be prepared by the processes of the present invention, these processes can be used to prepare a wide variety of useful organofunctional siloxanes. Such materials find use, for example, as wetting agents, thickeners, emulsifiers, antifoaming agents, urethane foam stabilizers for foams of various types (rigid, polyester, flexible polyether, frothed, high resiliency, semiflexible, microcellular, etc.), lubricants, aerosol shave cream stabilizers, and for other uses known for commercially available organofunctional siloxanes. For example, the chloroisobutyl-modified siloxanes disclosed herein are useful as surfactants for the preparation of high resilience polyurethane foams and are useful as intermediates for the preparation of non-hydrolyzable surfactants for flexible, polyester and rigid foams. The organofunctional siloxanes of this invention perform very well in water systems because they are nonhydrolyzable at the ≡SiC≡ bond connecting the functional group to silicon.

The organofunctional siloxanes of the present invention can be tailor-made to fit an intended application by choosing the particular structure of the organohydrosiloxane and the organic functional compound. Thus, the reactants can be chosen to obtain a product which finds use as an aqueous wetting agent. Another product can be useful as a surfactant for rigid polyurethane foam. Still another product can be useful as a surfactant for flexible polyether foam. Because of their hydrostable nature, they are useful in a variety of applications in which they come into contact with water or other protic solvents wherein prior hydrolyzable organic functional siloxanes would be unstable. These applications include aqueous foaming and thickening agents, water soluble lubricants, aqueous premixes for various types of urethane foams, aqueous emulsions, and the like.

The following examples are presented. The numbered examples illustrate this invention; the lettered examples are presented for comparison purposes and do not per se illustrate this invention. In the examples and throughout the specification, all temperatures are on the Centigrade scale, all percentages and parts are on a weight basis unless specified otherwise and the following abbreviations are used:

g denotes gram or grams
min. or mins. denote minute or minutes
hr. or hrs. denote hour or hours
ml. denotes milliliter
mm. denotes millimeters of mercury pressure
Ac denotes —COCH$_3$.
Me denotes methyl
D$_3$D' denotes heptamethylcyclotetrasiloxane:

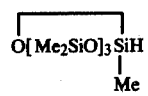

or the corresponding derivative thereof:

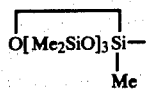

MD'M denotes heptamethyltrisiloxane:

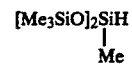

or the corresponding derivative thereof:

M$_3$T' denotes nonamethyltetrasiloxane: [Me$_3$SiO]$_3$SiH
MM' denotes the radical

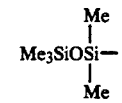

All reactions were run in standard laboratory glassware or flasks of various sizes as noted in each example using magnetic stirring under nitrogen atmosphere with heat being applied by electric mantles. Flasks were also fitted with Hopkins condensers and thermometers, temperatures being recorded in Centigrade. All reaction products were identified by vapor phase chromatography (VPC) and nuclear magnetic resonance (NMR) spectroscopy. Reported yields are based on the amount of hydrosiloxane charged.

EXAMPLE A

Reaction of D$_3$D' with methallyl chloride; reactants combined at start.

In a 200ml apparatus, there were combined 56.4g (0.2 mol) of D$_3$D', 20.0g (0.22 mol) of methallyl chloride, and 0.2 ml of a reduced platinum catalyst (prepared according to Example 1, U.S. Pat. No. 3,220,972). Heat was applied to about 80° C. when an exothermic reaction occurred to a maximum temperature of 141° C. Reaction was complete after 1 hr., 17 mins. and was followed by cooling. The reaction mixture was suction filtered into a 100 ml flask which was fitted for vacuum distillation. The following products were isolated:

| Product | Boiling point/pressure | g | Yield |
|---|---|---|---|
| D$_3$D'Cl | 76°/17mm (aspirator) | 17.0 | 27.0% |
| D$_3$D'CH$_2$C(CH$_3$) = CH$_2$ | 80°/17mm (aspirator) | 3.0 | 4.4% |
| D$_3$D'CH$_2$CH(CH$_3$)$_2$ | 80°/17mm (aspirator) | 1.6 | 2.4% |
| D$_3$D'CH$_2$CH(CH$_3$)CH$_2$Cl* | 60°/0.25mm | 44.8 | 60.0% |
| Heavies | — | 1.2 | — |

*The yield of the desired hydrosilation product by this route was 60.0%.

EXAMPLE 1

Reaction of D$_3$D' with methallyl chloride; olefin added to hydrosiloxane.

In a 500ml apparatus were placed 282g (1.0 mol) of D$_3$D' which was heated to 85° C., followed by addition of 0.3ml of a solution of 4.0 wt.% of H$_2$PtCl$_6$ . 6H$_2$O in 1,2-dimethoxyethane. Dropwise addition of 90.5g (1.0 mol) of methallyl chloride was begun and continued at a rate which maintained the reaction temperature at 87°–93° C. Addition was complete in 1.5 hr., and the reaction mixture was distilled directly, yielding the following products:

| Product | Boiling point/pressure | g | Yield |
|---|---|---|---|
| $D_3D'Cl$ | 77°/17mm (aspirator) | 55.0 | 17.4% |
| $D_3D'CH_2C(CH_3)=CH_2$ | 31°/0.2mm | trace | — |
| $D_3D'CH_2CH(CH_3)_2$ | 31°/0.2mm | 30.5 | 9.0% |
| $D_3D'CH_2CH(CH_3)CH_2Cl$* | 55°/0.12mm | 246.2 | 66.1% |
| Heavies | — | 11.0 | — |

*The yield of the desired hydrosilation product was 66.1%, a relative improvement of 10.2% over the 60.0% obtained in Example A.

EXAMPLE B

Reaction of MD'M with methallyl chloride; reactants combined at start.

In the apparatus of Example A, there were combined 43.1(0.194 mol) of MD'M, 19.0g (0.21 mol) of methallyl chloride, and 0.2ml of the catalyst used in Example A. Heat was applied to 94° C. at which point the reaction mixture was refluxing. The reflux temperature increased over 2 hrs. to 143° C. The product mixture was transferred to a 100ml flask and distilled, yielding the following products:

| Product | Boiling point/pressure | g | Yield |
|---|---|---|---|
| Unreacted MD'M | 41°/17mm (aspirator) | 5.9 | 13.7% |
| $M_2D'Cl$ | 50°/17mm (aspirator) | 16.5 | 32.3% |
| $M_2D'CH_2C(CH_3)=CH_2$ | 56°/17mm (aspirator) | 3.9 | 7.1% |
| $M_2D'CH_2CH(CH_3)_2$ | — | nil | — |
| $M_2D'CH_2CH(CH_3)CH_2Cl$* | 36°/0.3mm | 21.3 | 34.1% |
| Heavies | — | 2.2 | — |

*The yield of the desired hydrosilation product was 34.1% The yields obtained compare favorably with those reported by Davis (J. Org. Chem., 38, 838 (1973), which were: $M_2D'Cl(18\%)$, $M_2D'CH_2C(CH_3)=CH_2$ (9%), and $M_2D'CH_2CH(CH_3)CH_2Cl$ (34%) wherein the reactants were combined at the start.

EXAMPLE 2

Reaction of MD'M with methallyl chloride; olefin added to hydrosiloxane.

In a 100ml flask, there were placed 39.1g (0.176 mol) of MD'M which was heated to 75°, when 0.2ml of the catalyst used in Example 1 was added. Addition of 16.3g (0.18 mol) of methallyl chloride was begun, with reaction proceeding slowly for 30 mins., followed by an exothermic temperature rise to 119°. Reaction was complete after 1.5 hrs. from start of addition. Direct vacuum distillation yielded the following products:

| Product | Boiling point/pressure | g | Yield |
|---|---|---|---|
| $M_2D'Cl$ | 50°/17mm (aspirator) | 7.9 | 17.5% |
| $M_2D'CH_2C(CH_3)=CH_2$ | 31°/0.22mm | 0.7 | 1.4% |
| $M_2D'CH_2CH(CH_3)_2$ | 31°/0.22mm | 4.9 | 10.0% |
| $M_2D'CH_2CH(CH_3)CH_2Cl$* | 33°/0.18mm | 27.6 | 50.2% |
| Heavies | — | 3.7 | — |

*The yield of the desired hydrosilation product was 50.2%, a relative improvement of 47.2% over the 34.1% obtained in Example B, or the 34% reported by Davis.

EXAMPLE C

Reaction of $D_3D'$ with allyl chloride; reactants combined at start.

In a 100ml flask there were combined 62.0g of 90% $D_3D'$ (containing 0.2 mol of $D_3D'$), 17.0g (0.22 mol) of allyl chloride, and 0.3ml of the catalyst used in Example A. Heat was applied to reflux temperature which increased gradually from 68° C. to 125° C. over 1.5 hrs. The reaction mixture was suction filtered into a 100ml distillation flask and distilled, yielding the following products:

| Product | Boiling point/pressure | g | Yield |
|---|---|---|---|
| $D_3D'Cl$ | 33°/0.3mm | 37.8 | 59.7% |
| $D_3D'CH_2CH_2CH_3$ | 44°/0.3mm | 4.0 | 6.2% |
| $D_3D'CH_2CH_2CH_2Cl$* | 63°/0.2mm | 8.0 | 11.2% |
| $D_3D'CH_2CH_2CH_2D'D_3$ | 117°/0.25mm | 8.8 | 14.6% |
| Heavies | — | 2.4 | — |

*The yield of the desired hydrosilation product was only 11.2%.

EXAMPLE D

Reaction of $D_3D'$ with allyl chloride; olefin added to hydrosiloxane.

In the apparatus of Example C, there were placed 56.4g (0.2 mol) of $D_3D'$ which was heated to 78° C., when 0.2ml of the catalyst used in Example 1 was added. Dropwise addition of 15.3g (0.2 mol) of allyl chloride was begun and the reaction temperature was maintained at 95°–124° C. until completion (37 mins.). The reaction mixture was distilled, yielding the following products:

| Product | Boiling point/pressure | g | Yield |
|---|---|---|---|
| $D_3D'Cl$ | 27°/0.7mm | 22.0 | 34.8% |
| $D_3D'CH_2CH_2CH_3$ | 29°/0.7mm | 16.6 | 33.0% |
| $D_3D'CH_2CH_2CH_2Cl$* | 53°/0.2mm | 13.9 | 19.4% |
| $D_3D'CH_2CH_2CH_2D'D_3$ | — | trace | — |
| Heavies | — | 1.6 | — |

*The yield of the desired hydrosilation product was 19.4%, a 73.2% relative improvement over the 11.2% obtained in Example C.

EXAMPLE E

Reaction of $D_3D'$ with 3-chloro-1-butene; olefin added to hydrosiloxane.

In a 100ml flask there were placed 56.4g (0.2 mol) of $D_3D'$ which was heated to 85° C., when 0.15ml of the catalyst used in Example 1 was added. Dropwise addition of 18.1g (0.2 mol) of 3-chloro-1-butene was begun and continued over 45 mins. at 87°–90° C. Heating was continued up to 105° C. for an additional 50 mins. The reaction mixture was distilled, yielding the following products:

| Product | Boiling point/pressure | g | Yield |
|---|---|---|---|
| $D_3D'Cl$ | 22°/0.2mm | 33.9 | 53.6% |
| $D_3D'CH_2CH=CHCH_3$ | 33°/0.2mm | 2.2 | 3.3% |
| $D_3D'CH_2CH_2CH_2CH_3$ | 33°/0.2mm | 4.1 | 6.0% |
| $D_3D'CH_2CH_2CHClCH_3$* | 45°/0.2mm | 24.7 | 33.2% |
| Heavies | — | 2.4 | — |

*The yield of the desired hydrosilation product was 33.2%, or about half that obtained in Example 1, where the isomeric methallyl chloride was used as the olefinic reactant.

EXAMPLE F

Reaction of $D_3D'$ with vinylidene chloride; olefin added to hydrosiloxane.

In a 200ml flask, there were placed 56.4g (0.2 mol) of $D_3D'$ which was heated to 75° C., when 0.2ml of the catalyst used in Example 1 was added. Addition of 19.4g (0.2 mol) of vinylidene chloride was begun, with the reaction temperature being maintained at 75°–85° C. by recycling the olefin through the addition funnel. After 1 hr., an exothermic reaction to 150° C. occurred. Reaction was terminated after an additional 1.5 hrs., followed by distillation, which yielded the following products:

| Product | Boiling point/pressure | g | Yield |
|---|---|---|---|
| $D_3D'Cl$ | 23°/0.3mm | 30.9 | 48.8% |
| $D_3D'CH_2CH_3$ | 26°/0.3mm | 3.4 | 5.5% |
| $D_3D'CHClCH_3$ | 33°/0.3mm | 1.9 | 2.8% |
| $D_3D'CH_2CH_2D'D_3$ | 90°/0.25mm | 12.2 | 20.7% |
| Heavies | — | 11.0 | — |

*The yield of the desired hydrosilation product, $D_3D'CH_2CHCl_2$, was nil.

EXAMPLE G

Reaction of $D_3D'$ with 2-chloromethyl-3-chloro-1-propene; olefin added to hydrosiloxane.

In a 50ml flask were placed 22.6g (0.08 mol) of $D_3D'$ which was heated to 80° C., when 0.1ml of the catalyst used in Example 1 was added. Dropwise addition of 9.9g (0.08 mol) of 2-chloromethyl-3-chloro-1-propene was begun, causing an exothermic reaction to 140° C. Addition was completed in 17 mins. followed by heating at 108°–146° C. for 23 mins. Vacuum distillation of the reaction mixture yielded the following products:

| Product | Boiling point/pressure | g | Yield |
|---|---|---|---|
| $D_3D'Cl$ | 20°/0.35mm | 9.1 | 35.9% |
| $D_3D'CH_2C(CH_3)=CH_2$ | 40°/0.25mm | 0.2 | 0.9% |
| $D_3D'CH_2CH(CH_3)_2$ | 40°/0.25mm | 0.8 | 2.8% |
| $D_3D'CH_2CH(CH_3)CH_2Cl$ | 55°/0.2mm | 5.0 | 16.8% |
| $D_3D'CH_2CH(CH_2Cl)_2$* | 75°/0.15mm | 9.0 | 27.6% |
| Heavies | — | 2.4 | — |

*The yield of the desired hydrosilation product, $D_3D'CH_2CH(CH_2Cl)_2$, was 27.6%. This product, based on $CH_2=C(CH_2Cl)_2$, also known as methallyl dichloride, was obtained in less than half the yield of the product of Example 1, which was based on methallyl chloride.

EXAMPLE H

Reaction of $D_3D'$ with 2,3-dichloro-1-propene; olefin added to hydrosiloxane.

In a 100ml flask were placed 28.2g (0.1 mol) of $D_3D'$ which was heated to 65° C. when 0.05ml of the catalyst used in Example 1 was added. Dropwise addition of 11.1g (0.1 mol) of 2,3-dichloro-1-propene was begun at 90° C., causing a temperature rise to 173° C. in 9 mins. Addition was stopped with 5.3g of olefin remaining in the addition funnel, because consumption of $D_3D'$ was complete. The reaction mixture was distilled, and yielded the following products:

| Product | Boiling point/pressure | g | Yield |
|---|---|---|---|
| $D_3D'Cl$ | 27°/0.7mm | 19.0 | 59.9% |
| $D_3D'CH_2CH_2CH_3$ | 29°/0.7mm | 6.2 | 19.1% |
| $D_3D'CH_2CH_2CH_2Cl$ | 45°/0.25mm | 1.0 | 2.8% |
| Heavies | — | 3.5 | — |

The yield of the desired hydrosilation product, $D_3D'CH_2CHClCH_2Cl$, was nil.

EXAMPLE I

Reaction of $D_3D'$ with 3,4-dichloro-1-butene; olefin added to hydrosiloxane.

In a 500ml flask were placed 141.0g (0.5 mol) of $D_3D'$ which was heated to 80° C., when 0.3ml of the catalyst used in Example A was added. Dropwise addition of 62.5g (0.5 mol) of 3,4-dichloro-1-butene was begun and continued at a rate which maintained the reaction temperature at 90°–100° C. over 1 hr. The reaction mixture was suction filtered into a 250ml flask and vacuum distilled, yielding the following products:

| Product | Boiling point/pressure | g | Yield |
|---|---|---|---|
| $D_3D'Cl$ | 30°/0.3mm | 94.0 | 59.4% |
| $D_3D'CH_2CH=CHCH_3$ | 42°/0.25mm | 3.4 | 2.0% |
| $D_3D'CH_2CH_2CH_2CH_3$ | 42°/0.25mm | 19.3 | 11.4% |
| $D_3D'CH_2CH_2CHClCH_2Cl$* | 75°/0.25mm | 22.8 | 11.2% |
| $D_3D'(CH_2)_4D'D_3$ | 140°/0.4mm | 5.7 | 3.7% |
| Heavies | — | 22.3 | — |

*The yield of the desired hydrosilation product was 11.2%.

EXAMPLE J

Reaction of $D_3D'$ with 2-methyl-1-chloro-1-propene; olefin added to hydrosiloxane.

In a 100ml flask were placed 56.4g (0.2 mol) of $D_3D'$ which was heated to 80° C., when 0.2ml of the catalyst used in Example 1 was added. Dropwise addition of 18.1g (0.2 mol) of 2-methyl-1-chloro-1-propene was begun, causing an exothermic reaction with a maximum temperature of 142° C. during addition, which required 45 mins. The reaction mixture was distilled, yielding the following products:

| Product | Boiling point/pressure | g | Yield |
|---|---|---|---|
| $D_3D'Cl$ | 75°/17mm (aspirator) | 29.4 | 46.4% |
| $D_3D'CH_2CH(CH_3)_2$ | 33°/0.2mm | 25.3 | 37.4% |
| $D_3D'CH_2CH(CH_3)CH_2Cl$* | 60°/0.25mm | 3.0 | 4.0% |
| Heavies | — | 2.0 | — |

*The yield of $D_3D'CH_2CH(CH_3)CH_2Cl$ which was obtained (4.0%) is attributed to 2-methyl-3-chloro-1-propene (methallyl chloride) which was present as an impurity (4.5% level) in the isomeric 2-methyl-1-chloro-1-propene starting material. The yield of desired hydrosilation product was nil.

EXAMPLE K

Reaction of $D_3D'$ with vinyl acetate; olefin added to hydrosiloxane.

In a 200ml flask were placed 70.5g (0.25 mol) of $D_3D'$ which was heated to 95° C., when 0.2ml of the catalyst used in Example A was added. The dropwise addition of 21.5g (0.25 mol) of vinyl acetate was begun and completed in 15 mins. Reaction was allowed to continue up to 140° C. in 22 hrs. The reaction mixture was suction filtered into a 100ml distillation flask and distilled, yielding the following products:

| Product | Boiling point/pressure | g | Yield |
|---|---|---|---|
| $D_3D'CH_2CH_3$ | 80°/17mm (aspirator) | 14.6 | 18.9% |
| $D_3D'OAc$ | 51°/5.0mm | 19.3 | 22.7% |
| $D_3D'CH(CH_3)OAc$ | 55°/4.0mm | 30.7 | 33.4% |
| $D_3D'CH_2CH_2OAc$* | 65°/4.0mm | 7.9 | 8.6% |
| Heavies | — | 11.0 | — |

*The yield of the desired hydrosilation product, $D_3D'CH_2CH_2OAc$, was obtained in 8.6% yield, while an unexpected isomeric product, $D_3D'CH(CH_3)OAc$, was obtained in 33.4% yield for a combined total of 42.0%.

EXAMPLE L

Reaction of $D_3D'$ with allyl acetate; reactants combined at start.

In a 100ml flask were combined 28.2g (0.1 mol) of $D_3D'$, and 10.5g (0.105 mol) of allyl acetate. Heat was applied to 81.5° C. and 0.05ml of the catalyst used in Example A was added. There was a violent and rapid exothermic reaction to 154° C. in 1 min. The reaction mixture was allowed to cool to 120° C. in 1 hr. After further rapid cooling, the reaction mixture was suction filtered into a 100ml distillation flask and distilled, yielding the following products:

| Product | Boiling point/pressure | g | Yield |
| --- | --- | --- | --- |
| $D_3D'OAc$ | 35°/0.34mm | 11.7 | 35.3% |
| $D_3D'CH_2CH_2CH_3$ | 35°/0.34mm | 1.6 | 5.0% |
| $D_3D'CH_2CH_2CH_2OAc$* | 70°/0.3mm | 18.2 | 47.6% |
| Heavies | — | 1.0 | — |

*The yield of the desired hydrosilation product was 47.6%.

EXAMPLE M

Reaction of $D_3D'$ with isopropenyl acetate; reactants combined at start.

In a 200ml flask were combined 70.5g (0.25 mol) of $D_3D'$ and 25.0g (0.25 mol) of isopropenyl acetate (2-acetoxypropene). Heat was applied to 36° C. and 0.2ml of the catalyst used in Example A was added. There was a slow exothermic reaction to 138° in 40 mins. After an additional hour, the reaction mixture was cooled and distilled yielding the following products:

| Product | Boiling point/pressure | g | Yield |
| --- | --- | --- | --- |
| $D_3D'OAc$ | 39°/4.0mm | 58.4 | 68.7% |
| $D_3D'CH_2CH_2CH_3$ | 39°/4.0mm | 17.9 | 22.1% |
| $D_3D'CH_2CH(CH_3)OAc$* | 90°/4.0mm | 2.9 | 3.0% |
| Heavies | — | 2.4 | — |

*The yield of the desired hydrosilation product was only 3.0%.

EXAMPLE 3

Reaction of $D_3D'$ with methallyl acetate; reactants combined at start.

In a 100ml flask were combined 30.2g of 90% $D_3D'$ (0.1 mol $D_3D'$) and 12.0g (0.105 mol) of methallyl acetate. Heat was applied to 80° C. and 0.2ml of the catalyst used in Example A was added. There was an immediate exothermic reaction to 164° C. in 1.5 mins. The reaction mixture was suction filtered into a 50ml distillation flask and distilled, yielding the following products:

| Product | Boiling point/pressure | g | Yield |
| --- | --- | --- | --- |
| $D_3D'OAc$ | — | nil | — |
| $D_3D'CH_2CH(CH_3)CH_2OAc$* | 80°/0.3mm | 36.4 | 92.0% |
| Heavies | — | 1.3 | — |

*The yield of the desired hydrosilation product was 92.0%, considerably higher than that of Examples K (42.0%), L (47.6%), or M (3.0%).

EXAMPLE N

Reaction of MD'M with vinyl acetate; reactants combined at start.

In a 100ml flask were combined 55.5g (0.25 mol) of MD'M, 21.5g (0.25 mol) of vinyl acetate, and 0.3ml of the catalyst used in Example A. Heat was applied to reflux (87° C.) and the temperature allowed to increase to 130° C. by recycling vinyl acetate through an addition funnel over 7 hrs. The reaction mixture was suction filtered into a 100ml distillation flask and distilled, yielding the following products:

| Product | Boiling point/pressure | g | Yield |
| --- | --- | --- | --- |
| $M_2D'CH = CH_2$ | 50°/17mm (aspirator) | 0.7 | 1.1% |
| $M_2D'CH_2CH_3$ | 50°/17mm (aspirator) | 5.9 | 9.4% |
| $M_2D'OAc$ | 72°/17mm (aspirator) | 15.8 | 22.6% |
| $M_2D'CH(CH_3)OAc$* | 95°/17mm (aspirator) | 7.7 | 10.0% |
| $M_2D'CH_2CH_2OAc$* | 55°/2.5mm | 18.9 | 24.6% |
| $M_2D'CH_2CH_2D'M_2$ | 85°/3.0mm | 7.9 | 13.4% |
| Heavies | — | 9.5 | — |

*The desired hydrosilation product was obtained as a mixture of two isomers having a combined yield of 34.6%.

EXAMPLE 4

Reaction of MD'M with methallyl acetate; reactants combined at start.

In a 100ml flask were combined 8.5g (0.074 mol) of methallyl acetate, and 15.5g (0.07 mol) of MD'M. Heat was applied to 81° C. and 0.1ml of the catalyst used in Example A was added. Heating was continued up to 113° C. over a period of 18 mins. when an exothermic reaction to 137° C. occurred. Heating was continued up to 166° C. over 2 hrs. and 40 mins. The reaction mixture was suction filtered into a 50ml distillation flask and distilled, yielding the following products:

| Product | Boiling point/pressure | g | Yield |
| --- | --- | --- | --- |
| $M_2D'OAc$ | 72°/17mm (aspirator) | 0.6 | 3.0% |
| $[(CH_3)_3SiO]_3SiH, M_3T'$ | 80°/17mm (aspirator) | 0.6 | 3.0% |
| $MM'CH_2CH(CH_3)CH_2OAc$ | 65°/0.4mm | 0.7 | 3.0% |
| $M_2D'CH_2CH(CH_3)CH_2OAc$* | 74°/0.3mm | 15.8 | 67.2% |
| Heavies | — | 1.2 | — |

*The yield of the desired hydrosilation product, 67.2% was almost double that obtained in the MD'M - vinyl acetate reaction of Example N. The $M_3T'$ and $MM'CH_2CH(CH_3)$-$CH_2OAc$ [latter is $(CH_3)_3SiOSi(CH_3)_2CH_2CH(CH_3)CH_2OAc$] are products from a well-known re-arrangement of MD'M (see J. Org. Chem., 30, 1651 (1965)).

EXAMPLE 5

Reaction of $D_3D'$ with methallyl methacrylate; hydrosiloxane added to olefin.

In this reaction, a reverse mode of addition is employed to prevent polymerization of methacrylate groups under hydrosilation conditions. In a 100ml flask were placed 21.0g (0.15 mol) of freshly distilled methallyl methacrylate (containing 0.1g phenothiazine inhibitor), and 2.0ml of the catalyst used in Example 1. Heat was applied to 50° C., and addition of 42.3g (0.15 mol) of $D_3D'$ begun. A gentle exotherm occurred up to 83° C., with addition of $D_3D'$ being completed in 30 mins. The reaction mixture was vacuum distilled, yielding the following products:

| Product | Boiling point/pressure | g | Yield |
| --- | --- | --- | --- |
| $D_3D'CH_2CH(CH_3)CH_2O_2C(CH_3) = CH_2$* | 90°/0.25mm | 37.6 | 59.4% |
| $D_3D'CH_2CH(CH_3)CO_2CH_2C(CH_3) = CH_2$ | 90°/0.25mm | 3.3 | 5.2% |
| $D_3D'CH_2CH(CH_3)CH_2O_2CCH(CH_3)CH_2D'D_3$ | — | 15.8 | 25.0% |

*The yield of the desired monohydrosilation product, i.e., the monoadduct hydrosilated at the methallyl group, was 59.4%. Hydrosilation also occurred to a significant extent at the methacrylate group, yielding an isomeric monoadduct and diadduct.

EXAMPLE O

Reaction of $D_3D'$ with allylidene diacetate; olefin added to hydrosiloxane.

In a 100ml flask were placed 28.2g (0.1 mol) of $D_3D'$ which was heated to 84° C., when 0.1ml of the catalyst used in Example 1 was added. Dropwise addition of 15.8g (0.1 mol) of allylidene diacetate was begun, causing an exotherm to 116° C. in 15 mins., when addition was complete. The reaction mixture was heated up to 122° C. for 15 more mins., followed by distillation, which yielded the following products:

| Product | Boiling point/pressure | g | Yield |
|---|---|---|---|
| $D_3D'OAc$ | 30°/0.3mm | 8.0 | 23.4% |
| $D_3D'CH(OAc)CH_2CH_3$ | 55°/0.3mm | 5.9 | 15.4% |
| $D_3D'CH_2CH_2CH(OAc)_2$* | 90°/0.25mm | 21.5 | 49.1% |
| Heavies | — | 1.7 | — |

*The yield of the desired hydrosilation product was 49.1%.

EXAMPLE 6

Reaction of $D_3D'$ with methallylidene diacetate; olefin added to hydrosiloxane.

In a 250ml flask were placed 42.4g (0.15 mol) of $D_3D'$ which was heated to 92° C., when 0.15ml of the catalyst used in Example 1 was added. Dropwise addition of 27.1g (0.158 mol) of methallylidene diacetate was begun and completed in 23 mins. causing a gentle exotherm to 118° C. The reaction mixture was transferred to a 150ml flask and distilled, yielding the following products:

| Product | Boiling point/pressure | g | Yield |
|---|---|---|---|
| $D_3D'OAc$ | 35°/0.35mm | 0.4 | 0.8% |
| $D_3D'CH_2CH(CH_3)CH(OAc)_2$* | 106°/0.35mm | 63.7 | 93.5% |

*The yield of the desired hydrosilation product was 93.5%, almost double that of Example O, where allylidene diacetate was used.

EXAMPLE P

Reaction of MD'M with allylidene diacetate, olefin added to hydrosiloxane.

In a 100ml flask were placed 21.5g (0.1 mol) of MD'M which was heated to 95° C., when 0.15ml of the catalyst used in Example A was added. Dropwise addition of 15.8g (0.1 mol) of allylidene diacetate was begun and was completed in 13 mins. causing an exotherm to 125° C. The reaction mixture was suction filtered into a 50ml distillation flask, and distilled, yielding the following products:

| Product | Boiling point/pressure | g | Yield |
|---|---|---|---|
| $M_2D'OAc$ | 70°/17mm (aspirator) | 12.6 | 45.0% |
| $M_2D'CH_2CH = CHOAc$ | 60°/0.25mm | 1.3 | 4.0% |
| $M_2D'CH_2CH_2CH(OAc)_2$* | 75°/0.25mm | 14.5 | 39.0% |
| Heavies | — | 0.6 | — |

*The yield of the desired hydrosilation product was 39.0%.

EXAMPLE 7

Reaction of MD'M with methallylidene diacetate; olefin added to hydrosiloxane.

In a 100ml flask were placed 32.3g (0.15 mol) of MD'M which was heated to 80° C., when 01.1ml of the catalyst used in Example A was added. Dropwise addition of 25.8g (0.15 mol) of methallylidene diacetate was begun and completed in 30 mins. There was an eventual exotherm to 127° C. after an additional 20 mins. followed by heating at 117°–127° C. for another 50 mins. The reaction mixture was distilled, yielding the following products:

| Product | Boiling point/pressure | g | Yield |
|---|---|---|---|
| $M_2D'OAc$ | 35°/0.35mm | 1.4 | 3.3% |
| $M_2D'CH_2CH(CH_3)CH(OAc)_2$* | 90°/0.3mm | 45.7 | 78.7% |
| Heavies | — | 2.9 | — |

*The yield of the desired hydrosilation product was 78.7%, double that of Example P, where allylidene diacetate was used.

EXAMPLE 8

Reaction of $D_3D'$ with methallyl carbamate; hydrosiloxane added to olefin.

The reverse mode of addition was employed in this example since methallyl carbamate is a solid. In a 100ml flask were combined 11.5g (0.1 mol) of methallyl carbamate and 40ml of toluene. The mixture was heated to 85° C. when 0.2ml of the catalyst used in Example 1 was added. Dropwise addition of 28.6g (0.1 mol) of $D_3D'$ was begun and completed in 14 mins. with continuous heating. The reaction temperature reached 120° C. after 45 more mins. of heating and finally reacted exothermically after an additional 25 mins. The reaction mixture was suction filtered into a 100ml distillation flask, and distilled, yielding the following products:

| Product | Boiling point/pressure | g | Yield |
|---|---|---|---|
| $D_3D'CH_2CH(CH_3)CH_2O_2CNH_2$* | 120°/0.32mm | 26.9 | 87.0% |
| Heavies | — | 2.7 | — |

*The yield of the desired hydrosilation product was 87%.

EXAMPLE 9

Reaction of MD'M with methallyl carbamate; hydrosiloxane added to olefin.

In the apparatus of Example 8 were combined 11.5g (0.1 mol) of methallyl carbamate and 40ml toluene. Heat was applied to 88° C. and 0.2ml of the catalyst used in Example 1 was added. Dropwise addition of 21.7g (0.1 mol) in MD'M was begun and completed in 37 mins. with continuous heating, followed by additional heating at 114°–118° C. for 70 mins. The reaction mixture was suction filtered into a 100ml flask, and distilled yielding the following products:

| Product | Boiling point/pressure | g | Yield |
|---|---|---|---|
| $M_2D'NHCO_2CH_2C(CH_3) = CH_2$ | 75°/0.3mm | 0.7 | 2.1% |
| $M_2D'NHCO_2CH_2CH(CH_3)_2$ | 75°/0.3mm | 0.4 | 1.2% |
| $M_2D'CH_2CH(CH_3)CH_2O_2CNH_2$* | 110°/0.3mm | 22.7 | 67.4% |
| Heavies | — | 2.1 | — |

*The desired hydrosilation product was obtained in 67.4% yield which compares favorably with the 67.2% yield obtained from the MD'M-methallyl acetate reaction of Example 4.

EXAMPLE 10

Reaction of $D_3D'$ with allyl methyl ether; reactants combined at start.

In a 200ml flask were combined 42.4g (0.15 mol) of $D_3D'$, 11.9g (0.156 mol) of allyl methyl ether, and 18.1g toluene. Heat was applied to 60° C. and 0.1ml of the catalyst used in Example A was added. There was an exothermic reaction from 60°–93° C. After 1 hr., reaction was 70% complete. Distillation yielded 55% (25.1g) of the desired hydrosilation product, $D_3D'CH_2CH_2CH_2OCH_3$, as the only product, boiling point, 58°/1.0mm.

EXAMPLE 11

Reaction of $D_3D'$ with methallyl methyl ether; reactants combined at start.

In the apparatus of Example 10 were combined 42.4g (0.15 mol) of $D_3D$; 14.2g (0.165 mol) of methallyl methyl ether, and 18.9g toluene. Heat was applied to 60° C. and 0.1ml of the catalyst used in Example A was added. There was a rapid exothermic reaction which reaised the temperature from 60° to 128° C., with reaction being completed in 1 hr. Distillation yielded 90.2% (48.9g) of the desired hydrosilation product, $D_3D'CH_2CH(CH_3)CH_2OCH_3$, boiling point, 83°/1.0mm. The yield was considerably higher than that of Example 10 due to more complete reaction in the same time period.

EXAMPLE 12

Reaction of $D_3D'$ with 3-allyloxypropionitrile; reactants combined at start.

In a 100ml flask were combined 28.2g (0.1 mol) of $D_3D'$ and 11.1g (0.1 mol) of 3-allyloxypropionitrile. Heat was applied to 91° C. and 0.05ml of the catalyst used in Example A was added. There was an instantaneous exothermic reaction from 91° C. to 187.5° C. Distillation of the reaction mixture yielded 80% (31.2g) of the desired hydrosilation product, $D_3D'CH_2CH_2CH_2OCH_2CH_2CN$, boiling point, 98°/0.22mm.

EXAMPLE 13

Reaction of $D_3D'$ with 3-methallyloxypropionitrile; reactants combined at start.

In the apparatus of Example 12 were combined 28.2g (0.1 mol) of $D_3D'$ and 12.5g (0.1 mol) of 3-methallyloxypropionitrile. Heat was applied to raise the temperature to 90° C. and 0.05ml of the catalyst used in Example A was added. There was an immediate exothermic reaction from 90° C. to 179° C. Distillation yielded 90.2% (36.7g) of the desired hydrosilation product, $D_3D'CH_2CH(CH_3)CH_2OCH_2CH_2CN$, boiling point, 105°/0.22mm.

EXAMPLE 14

Reaction of $D_3D'$ with allyl cyanide; reactants combined at start.

In a 250ml flask were combined 42.4g (0.15 mol) of $D_3D'$ and 10.6g (0.158 mol) of allyl cyanide. Heat was applied to 63° C. and 0.1ml of the catalyst used in Example A was added. With continuous heating at 63°–100° C. over 2 hrs., the reaction was 97% complete. Distillation yielded 86.7% (45.4g) of a mixture containing mainly the desired hydrosilation product, $D_3D'CH_2CH_2CH_2CN$, boiling point, 132°/1.0mm and apparently containing the isomeric products, $D_3D'CH(CH_3)CH_2CN$ and $D_3D'CH(CN)CH_2CH_3$.

EXAMPLE 15

Reaction of $D_3D'$ with methallyl cyanide; reactants combined at start.

In the apparatus of Example 14 were combined 54.7g (0.194 mol) of $D_3D'$ and 16.2g (0.2 mol) of methallyl cyanide. Heat was applied to 64° C. and 0.2ml of the catalyst used in Example A was added. There was a gradual exothermic reaction from 64° C. to 118° C. After 2 more hrs. at 90°–118° C., the reaction was 77% complete. Distillation yielded 50.3g (71%) of the desired hydrosilation product, $D_3D'CH_2CH(CH_3)CH_2CN$, boiling point, 110°/0.7mm. While the comparative data from Examples 14 and 15 might indicate a higher yield for allyl cyanide over methallyl cyanide, it was later found that the methallyl cyanide used in Example 14 contained significant amounts of an unreactive isomer, senecionitrile $((CH_3)_2C = CHCN)$, such that the yield based on the contained amount of methallyl cyanide was higher than that based on allyl cyanide.

EXAMPLE 16

Reaction of $D_3D'$ with allyl alcohol; olefin added to hydrosiloxane.

In a 100ml flask were placed 30.2g of 90% $D_3D'$ (0.1 mole $D_3D'$) which was heated to 50° C., when 0.1ml of the catalyst used in Example A was added. Dropwise addition of 6.2g (0.11 mol) of allyl alcohol was begun, causing a rapid exotherm to 122° C. Addition was complete in 12 mins., as was the reaction. The reaction mixture was transferred to a 50ml flask and distilled, yielding the following products:

| Product | Boiling point/pressure | g | Yield |
|---|---|---|---|
| $D_3D'OCH_2CH_2CH_3$ | 41°/0.25mm | 2.1 | 6.2% |
| $D_3D'CH_2CH_2CH_2OH$* | 71°/0.25mm | 24.1 | 71.0% |
| $D_3D'CH_2CH_2CH_2OD'D_3$ | 116°/0.22mm | 4.4 | 13.6% |
| Heavies | — | 1.0 | — |

*The yield of the desired hydrosilation product, $D_3D'CH_2CH_2CH_2OH$, was 71.0%, and was reduced somewhat by the concurrent formation of a diadduct, $D_3D'CH_2CH_2CH_2OD'D_3$.

EXAMPLE 17

Reaction of $D_3D'$ with methallyl alcohol, olefin added to hydrosiloxane.

In the apparatus of Example 16 were placed 30.2g of 90% $D_3D'$ (0.1 mol $D_3D'$) which was heated to 51° C. when 0.1ml of the catalyst used in Example A was added. Dropwise addition of 7.6g (0.106 mol) of methallyl alcohol was begun and completed in 7 mins., followed by a rapid exothermic reaction to 134.5° C. The reaction mixture was suction filtered into a 50ml flask and distilled, yielding the following products:

| Product | Boiling point/pressure | g | Yield |
|---|---|---|---|
| $D_3D'OCH_2CH(CH_3)_2$ | 45°/0.3mm | 0.4 | 1.0% |
| $D_3D'CH_2CH(CH_3)CH_2OH$* | 80°/0.25mm | 30.4 | 87.0% |
| Heavies | — | 2.9 | — |

*The yield of the desired product, 87.0%, was somewhat higher than that of Example 16 (71.0%), with much less diadduct formation.

EXAMPLE 18

Reaction of MD'M with methallyl alcohol; olefin added to hydrosiloxane.

In a 200ml flask were placed 97.6g (0.44 mol) of MD'M which was heated to 54° C. when 0.15ml of the catalyst used in Example 1 was added. Dropwise addition of 33.1g (0.46 mol) of methallyl alcohol was begun causing an exotherm to 150° C. with complete reaction in 40 mins. The reaction mixture was suction filtered into a 200ml flask and distilled, yielding the following products:

| Product | Boiling point/pressure | g | Yield |
|---|---|---|---|
| $(CH_3)_3SiOH$ | 25°/17mm (aspirator) | 67.9 | 52.5% |
| $(CH_3)_3SiOSi(CH_3)_3$ / O \| \| / $CH_2$  $CH_2$ \ / CH \| $CH_3$ | 59°/17mm (aspirator) | | |
| $M_2D'CH_2CH(CH_3)CH_2OH^*$ | 70°/0.45mm | | |
| Heavies | — | 58.1 | — |

*It became obvious during distillation that the desired product, $M_2D'CH_2CH(CH_3)CH_2OH$, was decomposing at the distillation temperature, yielding trimethylsilanol and the heterocyclic disiloxane shown. The initial yield of $M_2D'CH_2CH(CH_3)CH_2OH$ is estimated to have been nearly 90%.

EXAMPLE Q

Reaction of $D_3D'$ with methallyl chloride; hydrosiloxane added to olefin.

In a 50ml. apparatus were placed 9.1g (0.1 mol) of methallyl chloride and 0.05 ml of the platinum catalyst described in Example 1. Heat was applied to reflux (71%) and 30.5g of 92% $D_3D'$ (0.1 mol $D_3D'$, 8% of $(Me_2SiO)_4$ wherein Me is methyl) was added dropwise over 160 mins. The reaction temperature, with external heating was increased to 94° C. over the same time, and was maintained at 94° C. for an additional 40 mins. Vacuum distillation of the reaction mixture yielded the following products:

| Product | Boiling point/Pressure | g | Yield |
|---|---|---|---|
| $D_3D'Cl$ | 26°/0.1mm | 15.3 | 48.2% |
| $D_3D'CH_2C(CH_3)=CH_2$ | 30°/0.1mm | 2.3 | 6.9% |
| $D_3D'CH_2CH(CH_3)_2$ | 30°/0.1mm | 1.3 | 3.8% |
| $D_3D'CH_2CH(CH_3)CH_2Cl^*$ | 50°/0.1mm | 12.6 | 33.9% |
| Heavies | — | 2.0 | — |

*The yield of the desired hydrosilation product was 33.9%, considerably lower than 66.1% of Example 1.

EXAMPLE R

Reaction with MD'M with methallyl chloride; hydrosiloxane added to olefin.

In a 100ml apparatus were placed 9.1g (0.1 mol) of methallyl chloride and 0.05 ml of the platinum catalyst described in Example 1. Heat was applied to 61° C. and 22.2g (0.1 mol) of MD'M was added over 160 mins. The reaction temperature was increased to 125° C. with external heating over the same time period. The reaction mixture was vacuum distilled, yielding the following products:

| Product | Boiling point/Pressure | g | Yield |
|---|---|---|---|
| $M_2D'Cl$ | 50°/17mm (aspirator) | 18.0 | 70.3% |
| $M_2D'CH_2C(CH_3)=CH_2$ | 56°/17mm (aspirator) | 1.9 | 6.9% |
| $M_2D'CH_2CH(CH_3)_2$ | 56°/17mm (aspirator) | 0.3 | 1.2% |
| $M_2D'CH_2CH(CH_3)CH_2Cl^*$ | 30°/0.04mm | 5.0 | 15.9% |
| Heavies | — | 0.9 | 2.9% |

*The yield of the desired hydrosilation product was 15.9%, considerably lower than the 50.2% of Example 2.

EXAMPLE S

Reaction of $D_3D'$ with allyl chloride; hydrosiloxane added to olefin.

In a 50ml apparatus were placed 7.7g (0.1 mol) of allyl chloride and 0.05 ml of the platinum catalyst described in Example 1. Heat was applied to 40° C. and 30.5g of 92% $D_3D'$ (0.1 mol $D_3D'$, 8% of $(Me_2SiO)_4$ wherein Me is methyl) was added over 83 mins. The reaction temperature was increased to 68° C. Heating was continued to 80° C. in 11 more mins., followed by an exothermic temperature rise to 119° C. in 7 mins. The reaction mixture was vacuum distilled, yielding the following products:

| Product | Boiling point/Pressure | g | Yield |
|---|---|---|---|
| $D_3D'Cl$ | 26°/0.4mm | 21.3 | 67.3% |
| $D_3D'CH_2CH_2CH_3$ | 34°/0.4mm | 2.9 | 8.9% |
| $D_3D'CH_2CH_2CH_2Cl^*$ | 56°/0.4mm | 4.9 | 13.5% |
| $D_3D'CH_2CH_2CH_2D'D_3$ | — | 1.5 | 5.0% |
| Heavies | — | 0.3 | 0.8% |

*The yield of the desired hydrosilation product was 13.5%, which was lower than 19.4% yield of Example D.

Throughout the specification and claims preferred monovalent hydrocarbon groups represented by R° are alkyl groups having 1 to 18 carbon atoms. As regards X, Y and Z, preferred hydrocarbonoxy groups are alkoxy groups having 1 to 18 carbon atoms, preferred cyanohydrocarbonoxy groups are cyanoalkoxy groups having 2 to 19 carbon atoms, preferred acyloxy groups are alkanoyloxy groups having 1 to 18 carbon atoms and preferred $-OC(O)NR_2$ groups are those in which R is hydrogen or alkyl having 1 to 18 carbon atoms or alkylene having 1 to 18 carbon atoms. Also, R' is preferably alkyl having 1 to 18 carbon atoms or aryl having 6 to 18 carbon atoms.

What is claimed is:

1. Process of making an organofunctional siloxane having bonded to silicon at least one monovalent group of the formula $$-CH_2CH(R°)CH_{3-m}X_m$$

wherein R° is a monovalent hydrocarbon group, X is a hydrocarbonoxy group, a cyanohydrocarbonoxy group, an acyloxy group, a halogen atom, a hydroxy group, a cyano group or a group having the formula $-OC(O)NR_2$ wherein R is a monovalent nitrogen-free organic radical, a divalent hydrocarbon group when both R's are taken together or hydrogen and may be the same or different throughout the same group or molecule, when X is halogen, hydroxy, cyano or a group of the formula $-OC(O)NR_2$, m is an integer of 1 and, when X is hydrocarbonoxy, cyanohydrocarbonoxy or acyloxy, m is 1 or 2, comprising subjecting a substituted allyl compound having the formula:

$$CH_2=C(R°)CH_{3-m}X_m$$

wherein X and m are as defined above and an organosiloxane having at least one silicon-bonded hydrogen to addition reaction conditions under which said silicon-bonded hydrogen and the silicon to which it is bonded become bonded respectively to the vicinal carbon atoms comprising the unsaturation of said substituted allyl compound, said organosiloxane and said substituted allyl compound having no groups that would interfere with said addition reaction and no groups, other than substituted allyl groups of said substituted allyl compound and silicon bonded hydrogen, that react under said addition reaction conditions, with the proviso that, when X is halogen, hydroxyl or cyano, the substituted allyl compound is added incrementally to said organosiloxane which is maintained at said addition reaction conditions.

2. Process as claimed in claim 1 for making an organofunctional siloxane containing one or more unit of the formula:

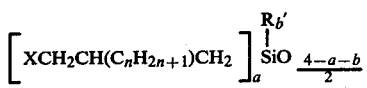

and having no other units or one or more unit of the formula:

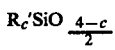

wherein X is as defined in claim 1, n is an integer of 1 to 18, R' is hydrogen or a monovalent hydrocarbon group which may be the same or different through the same unit or molecule, a is an integer of 1 to 3, b is an integer of 0 to 2, and c is an integer of 0 to 3, comprising reacting an alkallyl compound as defined in claim 1 wherein R° is —$C_nH_{2n+1}$- with a siloxane precursor having one or more unit of the formula:

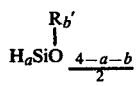

and having no other units or one or more unit of the formula:

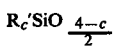

wherein R', a, b and c are as defined above to form said organofunctional siloxane.

3. Process as claimed in claim 2 wherein said alkallyl compound is added incrementally to said siloxane precursor.

4. Process as claimed in claim 2 wherein n is 1, a is 0 to 1, b is 1 to 2, a + b is 2 to 3, and c is 2 to 3.

5. Process as claimed in claim 2 wherein said alkallyl compound is a methallyl compound of the formula:

$$CH_2 = C(CH_3)CH_{3-m}X_m$$

wherein X and m are as defined in claim 1.

6. Process as claimed in claim 2 wherein X is chlorine, m is 1 and the alkallyl compound is methallyl chloride and said methallyl chloride is added incrementally to said organosiloxane.

7. Process as claimed in claim 6 wherein said organosiloxane is heptamethylcyclotetrasiloxane.

8. Process as claimed in claim 6 wherein said organosiloxane is heptamethyltrisiloxane.

9. Process as claimed in claim 2 wherein X is acetyl, m is 1 and the alkallyl compound is methallyl acetate.

10. Process as claimed in claim 9 wherein said organosiloxane is heptamethylcyclotetrasiloxane.

11. Process as claimed in claim 9 wherein said organosiloxane is heptamethyltrisiloxane.

12. Process as claimed in claim 2 wherein X is methacryloyl, m is 1 and the alkallyl compound is methallyl methacrylate.

13. Process as claimed in claim 12 wherein said organosiloxane is heptamethylcyclotetrasiloxane.

14. Process as claimed in claim 2 wherein X is acetyl, m is 2 and the alkallyl compound is methallylidene diacetate.

15. Process as claimed in claim 14 wherein said organosiloxane is heptamethylcyclotetrasiloxane.

16. Process as claimed in claim 14 wherein said organosiloxane is heptamethyltrisiloxane.

17. Process as claimed in claim 2 wherein X is carbamoyl, m is 1 and the alkallyl compound is methallyl carbamate.

18. Process as claimed in claim 17 wherein said organosiloxane is heptamethylcyclotetrasiloxane.

19. Process as claimed in claim 17 wherein said organosiloxane is heptamethyltrisiloxane.

20. Process as claimed in claim 2 wherein X is methoxy, m is 1, the alkallyl compound is methallyl methyl ether and said organosiloxane is heptamethylcyclotetrasiloxane.

21. Process as claimed in claim 2 wherein X is beta-cyanoethoxy, m is 1, the alkallyl compound is 3-methallyloxypropionitrile, and said organosiloxane is heptamethylcyclotetrasiloxane.

22. Process as claimed in claim 2 wherein X is cyano, m is 1, the alkallyl compound is methallyl cyanide, and said organosiloxane is heptamethylcyclotetrasiloxane.

23. Process as claimed in claim 2 wherein X is hydroxyl, m is 1, and the alkallyl compound is methallyl alcohol.

24. Process as claimed in claim 23 wherein said organosiloxane is heptamethylcyclotetrasiloxane.

25. Process as claimed in claim 23 wherein said organosiloxane is heptamethyltrisiloxane.

26. Process as claimed in claim 2 wherein said organosiloxane is heptamethylcyclotetrasiloxane.

27. Process as claimed in claim 2 wherein said organosiloxane is heptamethyltrisiloxane.

* * * * *